(12) United States Patent
Taff et al.

(10) Patent No.: US 11,097,114 B2
(45) Date of Patent: Aug. 24, 2021

(54) MODIFIED IMPLANTATION TOOL TIP CONFIGURATION FOR THE IMPROVED INSTALLATION OF LEADLESS PACEMAKERS WITH SHORT TINE-BASED ANCHORS

(71) Applicant: BIOTRONIK SE & Co. KG, Berlin (DE)

(72) Inventors: Brian M. Taff, Portland, OR (US); Dirk Muessig, West Linn, OR (US); Jeffrey A. von Arx, Lake Oswego, OR (US); Wantjinarjo Suwito, West Linn, OR (US); Larry Stotts, Tigard, OR (US); Andrew B. Kibler, Lake Oswego, OR (US); Eric Austin, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 369 days.

(21) Appl. No.: 15/683,191

(22) Filed: Aug. 22, 2017

(65) Prior Publication Data
US 2018/0071543 A1 Mar. 15, 2018

Related U.S. Application Data

(60) Provisional application No. 62/393,105, filed on Sep. 12, 2016.

(51) Int. Cl.
*A61N 1/375* (2006.01)
*A61N 1/05* (2006.01)
(Continued)

(52) U.S. Cl.
CPC ........ *A61N 1/37518* (2017.08); *A61B 5/6869* (2013.01); *A61M 25/008* (2013.01);
(Continued)

(58) Field of Classification Search
CPC ............ A61N 1/37518; A61N 1/37512; A61N 1/0573; A61N 1/059; A61N 1/3756;
(Continued)

(56) References Cited

U.S. PATENT DOCUMENTS 5,984,926 A 11/1999 Jones
6,559,416 B1 5/2003 Steenis et al.
(Continued)

FOREIGN PATENT DOCUMENTS

CN 201286706 Y 8/2009
GB 2 448 580 A 10/2008

OTHER PUBLICATIONS

European Search Report and Annex to the European Search Report on European Patent Application No. EP 16 20 2108.3, dated Jul. 26, 2017 (9 pages).

*Primary Examiner* — Katherine M Rodjom
(74) *Attorney, Agent, or Firm* — Buchanan Ingersoll & Rooney PC

(57) ABSTRACT

A system and method for installing/implanting a leadless implant can include a leadless implant with shortened tine-based anchors and an implantation tool with a modified tip. The tines can extend from a surface of the leadless implant and may include a preformed curve or other shape to enable the tine to hook into or grapple tissue. The implantation tool may be provided with a modified tip to assist with proper alignment, insertion, and anchoring of the shortened tines. A tip of the implantation tool can have a reduced inner diameter to cause the tine tips to be approximately normal to the surface of the tissue to which the implant is being anchored. Upon deployment of the leadless implant, the tines of the anchoring mechanism are appropriately aligned for proper insertion so that robust anchoring is achieved.

24 Claims, 7 Drawing Sheets

(51) Int. Cl.
*A61B 5/00* (2006.01)
*A61M 25/00* (2006.01)
*A61M 25/01* (2006.01)
*A61B 5/25* (2021.01)

(52) U.S. Cl.
CPC .... *A61M 25/0023* (2013.01); *A61M 25/0068* (2013.01); *A61M 25/0138* (2013.01); *A61N 1/059* (2013.01); *A61N 1/0573* (2013.01); *A61N 1/3756* (2013.01); *A61N 1/37512* (2017.08); *A61B 5/25* (2021.01); *A61B 2560/066* (2013.01); *A61B 2562/14* (2013.01); *A61B 2562/162* (2013.01); *A61M 2025/0081* (2013.01); *A61N 1/057* (2013.01); *A61N 2001/058* (2013.01); *A61N 2001/0582* (2013.01)

(58) Field of Classification Search
CPC .... A61N 1/057; A61B 5/6869; A61B 5/0408; A61M 25/0023; A61M 25/0068; A61M 25/008; A61M 25/0138
See application file for complete search history.

(56) References Cited

U.S. PATENT DOCUMENTS

| | | |
|---|---|---|
| 2004/0236311 A1 | 11/2004 | Ishii et al. |
| 2006/0074472 A1 | 4/2006 | Flach et al. |
| 2006/0241705 A1 | 10/2006 | Neumann et al. |
| 2008/0233787 A1 | 9/2008 | Geibel et al. |
| 2010/0179627 A1 | 7/2010 | Floyd et al. |
| 2010/0274074 A1* | 10/2010 | Khamis ............ A61B 17/00234 600/37 |
| 2010/0324644 A1 | 12/2010 | Levi et al. |
| 2011/0251660 A1 | 10/2011 | Griswold |
| 2011/0270339 A1 | 11/2011 | Murray, III et al. |
| 2012/0158111 A1 | 6/2012 | Khairkhahan et al. |
| 2012/0172892 A1* | 7/2012 | Grubac ................ A61N 1/3756 606/129 |
| 2014/0207149 A1 | 7/2014 | Hastings et al. |
| 2015/0051613 A1* | 2/2015 | Schmidt ............... A61N 1/3756 606/129 |
| 2015/0051616 A1* | 2/2015 | Haasl ................... A61N 1/0573 606/129 |
| 2018/0242960 A1* | 8/2018 | Kalloo ............... A61B 17/0057 |

* cited by examiner

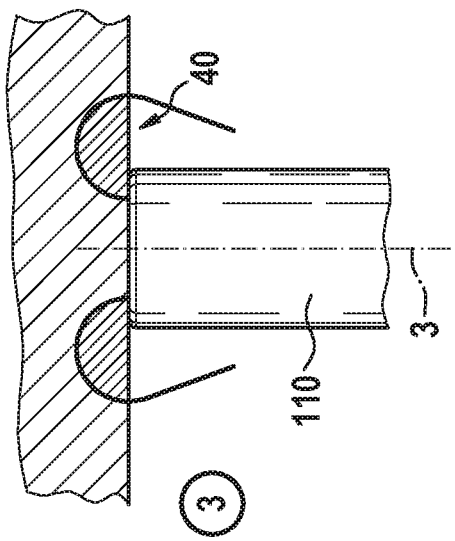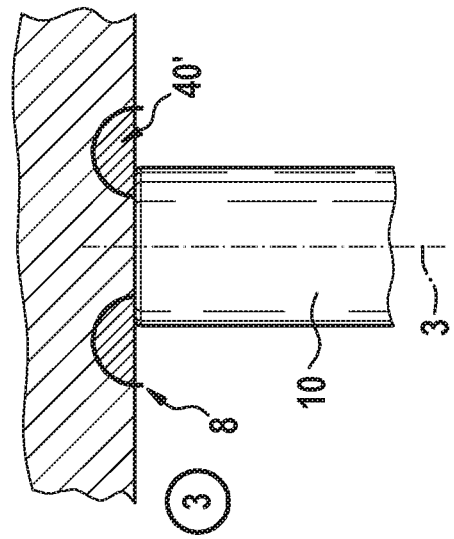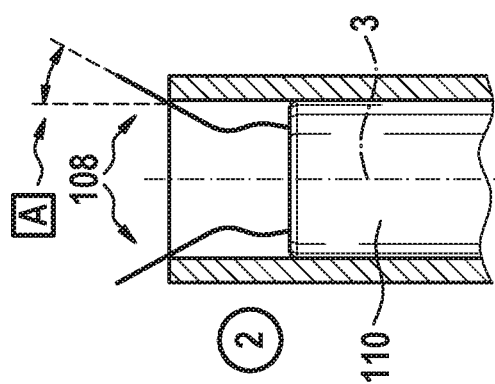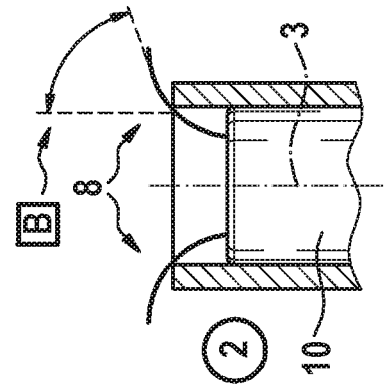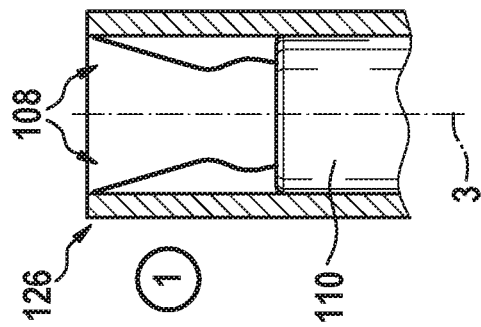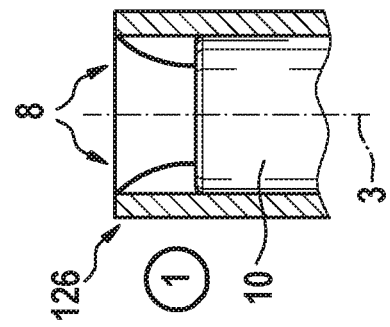
FIG. 5A Prior art
FIG. 5B

MODIFIED IMPLANTATION TOOL TIP CONFIGURATION FOR THE IMPROVED INSTALLATION OF LEADLESS PACEMAKERS WITH SHORT TINE-BASED ANCHORS

CROSS-REFERENCE TO RELATED APPLICATIONS

This patent application claims the benefit of U.S. Provisional Patent Application No. 62/393,105, filed on Sep. 12, 2016, which is hereby incorporated by reference in its entirety.

FIELD OF THE INVENTION

Various embodiments relate to a system and method for implanting a leadless medical implant with an improved anchoring mechanism and an improved implantation tool. In particular, the system can include an anchoring mechanism having shortened tines and an implantation tool with a modified tip to properly align the shortened tines.

BACKGROUND OF THE INVENTION

Fixation of leadless pacemakers or other implants to tissue typically requires a mechanical connection via an anchoring mechanism. Some anchoring mechanisms are attached to the implant, and thus connection via the anchoring mechanism secures the implant to the tissue. With tine-based anchors, the general methodology for implanting the implant typically demands or requires straightening of the tines using an affiliated implantation tool. The implantation tool can be a shroud-like tool or other tool to manipulate the tines so as to straighten them before fixation of the implant to the tissue. For example, the implantation tool can be in the form of a sleeve having an inner cavity to slidably receive the implant and cause the tines to straighten as they make contact with inner walls of the implantation tool. This straightening can be done to enforce or ensure tine alignment along an axis of the implant. Both the implant and implantation tool can then be placed against the tissue The tines may be subsequently inserted into the tissue by migrating or advancing the implant body toward, for example, the heart, where the implant is moved relative to the implantation tool. As the implantation body is advanced toward the tissue, the tines emerge from the implantation tool and their natural stiffness and preformed orientations may allow them to embed into the tissue (e.g., myocardium). The general trajectory of the tines through the myocardium generally depends upon two specific details: 1) the incidence angle at the moment the tine enters the tissue, and 2) the shape of the tine geometry itself.

With prior art tine-style anchor designs, the general tine geometry has leveraged or used a curved section near the locations where the tines emerge from the implant body followed by a more lengthy straightened section. The longer straightened section, when paired with the inner walls of the implantation tool's tip, generally serves to improve the incidence angle where the tines enter the patient's tissue. By virtue of this length and its interactions with the inner walls of the implantation tool, the tines can pierce far enough into the myocardium to "bite" into a substantial amount of the heart before the curved portions of the tines begin routing their trajectory back toward the implant. Such an approach may ensure robust mechanical anchoring, but is achieved at the expense of needing to employ longer tines than would prove essential if the tine/tissue incidence angle were more effectively managed. The present invention discloses a system and a method for using shortened tines and a modified implantation tool tip and, in particular, a modification to the inner walls of the implantation tool tip to better control this incidence angle while employing shortened tines.

Prior art methods and devices have exclusively employed geometries at the patient-facing terminus of the implantation tool that offer uniform inner diameters throughout the full length of the implantation tool and/or a catheter segment engaging with the implant. As such, to better approach piercing the myocardium along a surface that is normal to the direction of advancing the implant towards the tissue (i.e., a surface normal to the tissue), prior art anchor mechanisms have designed their tines to include lengthy straightened segments that, via spring action, hug the inner walls of the implantation tool. By hugging the inner walls of the implantation tool, these tines may be better oriented with the long axes of both the implant and implantation tool and thus enter the myocardium at a preferred angle.

However, the lengthy straightened segments of the prior art tine designs may complicate the routing of the implant from the inferior vena cava ("IVC") into the heart (since there is a longer rigid implant to make the bend), compete with opportunities to leverage or use device length as a means for provisioning added battery cell capacity, and enable a robust mechanical anchoring response at the expense of inflated or increased risks of perforation, tamponade, and/or stitching of the heart to the surrounding pericardial sac. Since leadless pacing already demands or requires unique installation procedures distinct from those associated with traditional leaded implanted pulse generators ("IPGs") (pocket-based), further confounding the implantation process (through implant anchoring mechanism and implantation tooling design interactions) is generally a suboptimal solution. Thus, an administering physician may have to, at best, execute an unnecessarily nuanced surgical procedures and, at worst, be forced to eliminate leadless therapeutic support as an option for certain patients based upon their internal physiology. At this point in their product maturity, it is unclear whether or not tine-based leadless pacemakers will always be explantable in chronic conditions. As such, compromising their available service life through ineffective anchor mechanism designs can force patients to undergo replacement therapies that promote the accumulation of abandoned in-body hardware sooner than necessary.

Leadless pacemakers should furthermore provide robust anchoring without presenting increased risks of perforation. While tine-based anchors have seemingly satisfied both of these criteria without reported clinical consequences, it is also commonly observed that perforations regularly occur. It is noted that such occurrences have thus far not created further challenges, yet avoiding perforations altogether through improved system designs would mitigate this potential for added complications entirely.

The present invention is directed toward overcoming one or more of the above-identified problems.

SUMMARY OF THE INVENTION

The system can include a leadless implant (also called "implant" in this disclosure) with an anchoring mechanism attached thereto and an implantation tool. The implant can be a leadless device like leadless pacemakers, or leadless capsules like sensors or small monitoring devices, which can be placed and/or attached and/or affixed on or within living bodies, for example, in or at organs like the heart, bodily cavities, or other tissue, having a casing to house electrical components, and may additionally house a battery. Extending from the casing can be the anchoring mechanism, which may include at least one tine. The tine may extend from a surface of the casing and may include a preformed curve or other two- or three-dimensional shape to enable the tine to hook into or grapple tissue to which the implant is to be anchored. While the inventive anchoring mechanism can be used to affix an implant to any type of tissue, the tissue referred to herein is generally myocardial tissue or epicardial tissue, unless otherwise specified. In some embodiments, the tines are of a length that is only necessary to provide secured anchoring. For example, prior art tines typically include use of tines having extended straight segments to assist with proper insertion but are otherwise undesirous and/or provide little to no additional utility. Instead, the disclosed system uses an implantation tool with a modified tip to assist with proper insertion and anchoring of shortened tines, where the shortened tines are of a length that is only necessary to provide secured anchoring.

The implantation tool may include a sleeve-like structure having an inner cavity that can slidably receive the implant. As the implant is received by the implantation tool, inner walls of the cavity can cause the shortened tines to flex and deviate from their preformed shape. A tip of the implantation tool can have an inner diameter that is less than the inner diameter of the rest of the cavity, where the reduced inner diameter to the implantation tool tip can cause the tine tips to be approximately normal to the surface of the tissue into which the implant is being anchored to. Thus, upon deployment of the implant the shortened tines of the anchoring mechanism can be made to be appropriately aligned for proper insertion and routing, while the length of the shortened tine provides adequate fixation without using surplus or redundant tine.

Current leadless pacemaker designs have adopted tine-based anchoring strategies that employ a series of nitinol tines that pierce into the tissue and, via spring force actuation, realize grappling hook configurations in deployed states. The presently disclosed invention improves upon this methodology by modifying the leading tip of the implantation tool to better orient the tines as they initially pierce patient tissue, and in particular better orient shortened tines. By forcing the shortened tines to enter the tissue along a surface normal to the direction of advancing the implant towards the tissue (i.e., a surface normal to the tissue), the invention provides a means to reduce the overall length of the tines that may be needed to safely anchor the implant to the tissue. Such benefits can ease or overcome procedural challenges associated with implantation procedures and robustly anchor (i.e., lower the risk of dislodgement) the implant in a manner that mitigates risks of perforation, tamponade, and/or stitching the heart to the pericardial sac.

The above-mentioned drawbacks of the prior art devices generally necessitate training for clinicians to ensure that clinicians can adequately manage the routing of longer than essential implants and/or implant anchors through the inferior vena cava ("IVC") and into the heart. Such training may require enhanced attention to procedural steps that, given the shorter anchoring format or configuration of the present invention, may prove to be unnecessary. Furthermore, the tine-style anchors of the prior art may increase the overall length of the implant in ways that produce additional challenges, which may include challenges related to the implant's ability to pair with certain patients. Determining which patients may or may not be eligible for such varieties of therapeutic support may in-turn necessitate additional pre-screening procedures, which may include calibrated imaging of patient vasculature, for example. The longer tines of prior art devices may also increase the need for follow-up caretaking in the event that vasculature in the vicinity of the IVC's interface with the right side of the heart is damaged during implantation. Further, longer tines may require more hardware to be untangled from the heart during attempts to chronically explant the implant. As such, it may be less feasible to explant implants, and in particular leadless pacemakers that employ lengthy tines. Thus, dedicated design efforts would, in-turn, prove increasingly essential to ensure that subsequent therapies (whether via traditional leaded pacers or the installation of additional leadless pacemakers) are viable. In cases where longer tines prohibit explantation and additional therapeutic hardware is implanted, physicians may incur increased responsibilities for adequately scrutinizing the appropriateness of magnetic resonance imaging ("MRI") and/or other potentially relevant diagnostic treatments.

Further, in case of a battery powered leadless implant, if less of the device length is consumed by the battery or allocated for the battery due to the lengthier tines, service times can be negatively affected. For example, implants are generally limited in length due to the fact that they are being implanted within a body of a patient, and in some cases attached to the heart. Decreasing tine length may allow the battery of the implant to be increased in length, thus providing more battery power. This means that the patient (with an implant having shorter battery) will be back in the clinic in need of a replacement device sooner than a patient receiving the same treatment but with a more substantial power source (with an implant having a longer battery). Facilitating the ability to incorporate longer batteries within the implants can soften the demand for power-efficient design development that squeezes component selection, inhibits chip foundry pairings, and may even impact feature availability and/or core performance capabilities.

In addition, longer tines have a tendency to cause tissue trauma at or near the implant site (e.g., the pacing site), increase the complexity of implantation tools In an exemplary embodiment, a leadless implant can include a casing having a casing distal end and a casing proximal end forming an axis that runs from the casing proximal end to the casing distal end, wherein the casing houses electrical components configured to provide electrical pulses to a heart/or to sense physiological signals from the mammal body; and an anchoring mechanism comprising at least one tine extending from a surface of the casing, leading to a curved segment, and then directly to a tine tip, wherein the at least one tine comprises a flexible, resilient material. The leadless implant may be configured to be inserted into an implantation tool having a cavity and an implantation tool tip both formed by an inner wall, wherein the inner wall at the implantation tool tip has an inner diameter of $D_1$ and the inner wall at the cavity has an inner diameter of $D_2$, wherein $D_1$ is less than $D_2$. $D_1$ causes the at least one tine to flex inward when a portion of the at least one tine makes contact with the inner wall for alignment of the at least one tine prior to contact with bodily tissue. The curved section of any tine can have at least one curve, which is at least segmentally formed in 3 dimensions. Any one tine can have a serpentine shape. Any one tine can have a spheroid shape tip. The curved segment of any one tine may form an approximate ninety-degree angle so that a portion of the tine leading to the tine tip extends radially outward from the axis. Any one tine may have a flared shape after the curved segment to cause the tine leading to the tine tip to flare away from the casing. The casing may additionally house a battery to supply electrical energy to the electrical components.

In an exemplary embodiment, an implantation tool can include a sleeve member having a cavity and a sleeve tip both formed by an inner wall, wherein the inner wall at the sleeve tip has an inner diameter of $D_1$ and the inner wall at the cavity has an inner diameter of $D_2$, wherein $D_1$ is less than $D_2$, wherein the implantation tool is configured to slidably receive a leadless implant through the cavity. This preferred embodiment presents a circumstance where the diameter of the implant, $D_{IMP}$, is larger than $D_1$ yet smaller than $D_2$ such that: $D_1 < D_{IMP} < D_2$. The leadless implant may include a leadless implant distal end and a leadless implant proximal end forming an axis that runs from the leadless implant proximal end to the leadless implant distal end; and, an anchoring mechanism comprising at least one tine extending from a surface of the leadless implant, leading to a curved segment, and then directly to a tine tip, wherein the at least one tine comprises a flexible, resilient material. $D_1$ causes the at least one tine to flex inward when a portion of the at least one tine makes contact with the inner wall for alignment of the at least one tine prior to contact with bodily tissue. The implantation tool may be at least a part of a catheter and connected to a catheter. The catheter may have a catheter tip that is rounded. Further, a transition from the $D_1$ to the $D_2$ may be smooth or stepped, with preferred embodiments offering a smooth, gradual transition between $D_1$ and $D_2$ on both the proximal and distal sides of the $D_1$ constriction. The ramped, smooth, and gradual transition between $D_1$ and $D_2$ on the patient-facing distal end of the catheter tip enables an ease in transitioning between tethered implant conditions and those where the implant fully resides within the tool while the ramping between the diameters further within the catheter tip (proximal) enables smooth tine and implant deployment operations. The inner wall of the sleeve tip may be formed by a double sided ramp forming the $D_1$ at a more constricted portion of the double sided ramp and forming the $D_2$ at a main diameter of the inner wall. The inner wall of the sleeve tip may be formed by a single sided ramp forming the $D_1$ at a more constricted portion of the double sided ramp and forming the $D_2$ at a main diameter of the inner wall. The inner wall of the sleeve tip may form $D_1$ and at least one slit extends radially from $D_1$ to a main diameter $D_2$. The inner wall of the sleeve tip can include at least one notch formed on a surface of the inner wall having $D_1$. The sleeve member can include a flexible, resilient material so that at least the inner wall of the sleeve tip is deflectable.

In an exemplary embodiment, a system for installation of a leadless implant may include a leadless implant comprising a casing having a casing distal end and a casing proximal end forming an axis that runs from the casing proximal end to the casing distal end, wherein the casing houses electrical components configured to provide electrical pulses to a heart/or to sense physiological signals from the mammal body; and, an anchoring mechanism comprising at least one tine extending from the surface of the casing, leading to a curved segment, and then directly to a tine tip, wherein the at least one tine comprises a flexible, resilient material. The system can further include an implantation tool comprising a sleeve member having a cavity and a sleeve tip both formed by an inner wall, wherein the inner wall at the sleeve tip has an inner diameter of $D_1$ and the inner wall at the cavity has an inner diameter of $D_2$, wherein $D_1$ is less than $D_2$, wherein the implantation tool is configured to slidably receive the leadless implant through the cavity, and wherein $D_1$ causes the at least one tine to flex inward when a portion of the at least one tine makes contact with the inner wall for alignment of the at least one tine prior to contact with bodily tissue. The casing of the leadless implant may additionally house a battery to supply electrical energy to the electrical components. The implantation tool may be at least a part of a catheter and connected to a catheter. The implantation tool can include a flexible, resilient material so that at least the inner wall of the sleeve tip is deflectable. The curved section of any tine can have at least one curve, which is at least segmentally formed in two or three dimensions. Further, any one tine may have a serpentine shape.

In an exemplary embodiment, a method for installation/implantation of a leadless implant may include choosing a jugular vein or femoral vein and opening the jugular or femoral vein to create a venous access through which a leadless implant is to be deployed; placing an introducer and passing through the leadless implant using a catheter via the introducer; determining an appropriate implant site using a fluoroscope; placing the implantation tool distal end against tissue of a heart so as to be normal to a surface of the tissue; advancing the leadless implant towards the tissue so as to cause the at least one tine tip to enter the tissue normal to the surface of the tissue; allowing the at least one tine to rebound to a preformed shape as it is inserted into the tissue due to further advancement of the leadless implant towards the tissue; tethering the leadless implant with a tether, including testing and confirming that a secure anchor has been achieved; removing the tether, the implantation tool, and the introducer from the venous access; and, closing the venous access.

While these potential advantages are made possible by technical solutions offered herein, they are not required to be achieved. The presently disclosed system and method can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following Figures, in which:

FIG. 5A shows a prior art implantation tool, a prior art implant, and prior art anchoring mechanism with long tines.

FIG. 5B shows a prior art implantation tool and an embodiment of the inventive implant having an embodiment of the inventive anchoring mechanism with short tines.

FIG. 6A shows the implant fully seated within the implantation tool and FIG. 6B shows the implant moving out from the implantation tool.

DETAILED DESCRIPTION OF THE INVENTION

The following description is of an embodiment(s) presently contemplated for carrying out the present invention. This description is not to be taken in a limiting sense, but is made merely for the purpose of describing the general principles and features of the present invention. The scope of the present invention should be determined with reference to the claims.

Figure 1:
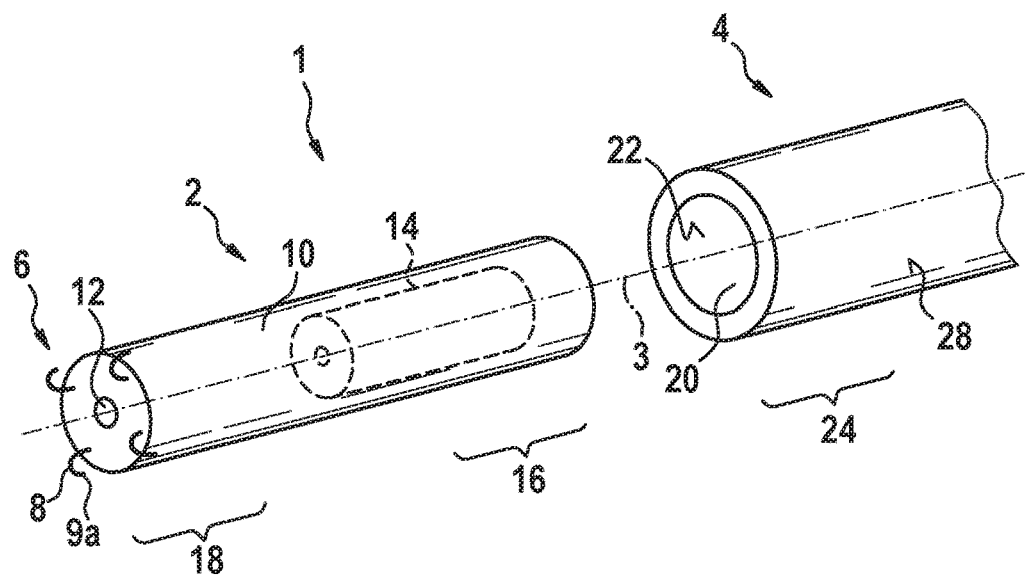
FIG. 1 is a perspective view of the system that may include an implant, an anchoring mechanism, and an implantation tool.

Referring to FIG. 1, the system 1 can include an implant 2 and an implantation tool 4. The implant 2 can have an anchoring mechanism 6, where the anchoring mechanism 6 may include at least one tine 8 attached to and extending from a surface of the implant 2. The implant can be a pacemaker, such as an implantable leadless pacemaker ("iLP"), or other leadless devices, for example capsules like sensors or small monitoring devices. These pacemakers or devices may be placed and/or attached and/or affixed on or within mammal organs, bodily cavities or other tissue. The tines 8 of the anchoring mechanism 6 are generally shorter than conventional tines used with similar implants, and are specifically configured to provide proper and aligned insertion through tissue and adequate securement of the implant 2 to tissue without providing surplus tine length. As will be explained in detail, use of shorter tines 8 can alleviate many of the surgical procedural problems associated with longer tines, as well as provide design benefits to the implant 2 itself.

The implant 2 can be a leadless pacemaker, which may include a casing 10 that houses electrical components (including an electrode 12), configured to provide electrical pulses to a heart, and a battery 14 to supply electrical energy to the electrical components. The casing 10 may be shaped to have an elongated shape (e.g., a cylinder) with an implant proximal end 16 and an implant distal end 18 forming an axis 3 that runs from the implant proximal end 16 to the implant distal end 18. The anchoring mechanism 6 is shown to be attached to and extend from the implant distal end 18; however, the anchoring mechanism 6 can be attached to and extend from any surface of the casing 10.

It is envisioned for three to four tines 8 to be used, but any number of tines 8 can be used. It is further envisioned for each tine 8 to be equidistally spaced about a perimeter edge of the casing distal end 18; however, the tines 8 can be positioned to extend from any casing 10 surface location and be separated by any distance, whether equally separated or not. Thus, the number of tines 8, the spacing of tines 8, and the placement of tines 8 can be varied to optimize the ability of the anchoring mechanism 6 to secure the implant 2 to the tissue. Further optimization factors may include reducing/increasing the number of tines 8, reducing/increasing the thickness of tines 8, spreading/narrowing the tines 8 apart so as to not interfere with electrode 12 of the implant 2 or other electrical components, etc.

The implantation tool 4 can be structured to slidably receive at least a portion of the implant 2. For example, the implantation tool 4 can be in a form of a sleeve having an inner cavity 20 to slidably receive the implant 2 and cause the tines 8 to straighten as they contact with inner wall 22 of the implantation tool 4. Thus, the implantation tool 4 can be a sleeve with a cavity 20 formed within an inner portion thereof, wherein the cavity 20 can be defined by a volume of space confined at least in part by the inner wall 22 of the sleeve. The implantation tool 4 can be cylindrical with an inner diameter and an outer diameter, wherein the outer wall has an outer diameter of "OD" and the inner wall has an inner diameter of "ID". It is envisioned for the implant 2 to be inserted into the cavity 20 of the implantation tool 4 so that the implant distal end 18 is most proximal to an implantation tool distal end 24. Thus, the implant 2 can be inserted so that the anchoring mechanism 6 can be most proximal to the implantation tool distal end 24. It is envisioned for the implant 2 to be inserted into the implantation tool 4 so that the implant 2, the tines 8, and the tine tips 9a are fully withdrawn into the cavity 20 (i.e., fully seated within the cavity 20). (See FIG. 6A). When fully seated, the inner wall 22 of the implantation tool 4 can cause the tines 8 of the anchoring mechanism 6 to straighten so as to be approximately parallel with the axis 3 of the implant 2.

In further embodiments, the inner wall 22 of the implantation tool 4 can cause the tines 8 of the anchoring mechanism 6 to straighten so that the tine tips 9a are approximately parallel with the axis 3 of the implant 2. During use, the implantation tool distal end 24 can then be placed against the tissue. If the tine tips 9a are receded too far into the cavity 20, the implant 2 can be advanced towards the tissue (moving the implant 2 relative to the implantation tool 4) so that the tine tips 9a make contact with the tissue. In other words, the implantation tool 4 can be caused to remain stationary while the implant 2 is advanced towards the tissue. The implant 2 can then be advanced further so that each tine 8 inserts into the tissue with the tine tips 9a spearheading the insertion. As the implant 2 is further advanced toward the tissue, the tines 8 and/or tine tips 9a can be caused to emerge from the implantation tool distal end 24 and begin to change orientation and direction. (See FIG. 6B). For example, each tine 8 can begin to reverting back to their preformed shape, thereby "hooking" into the tissue. (See FIG. 6C).

Figure 2:
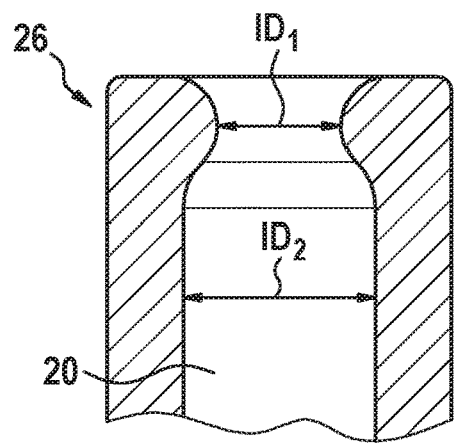
FIG. 2 is a partial cross-sectional view of an implantation tool tip that may be used with the inventive system.
Figure 8:
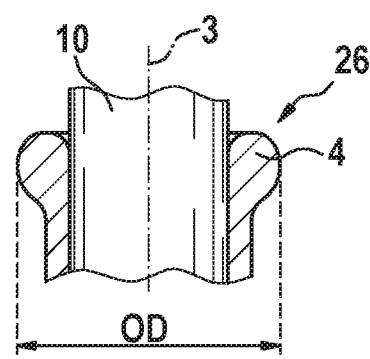
FIG. 8 is a partial cross-sectional view of an embodiment of an implantation tool tip, showing the flexible nature of the implantation tool tip where the implant body diameter, $D_{IMP}$, passes through the tool tip restriction.

Referring to FIG. 2, the implantation tool distal end 24 can include a specifically configured implantation tool tip 26 (i.e., a modified implantation tool tip configuration) that may facilitate proper alignment of the tines 8 and improved anchoring of the implant 2 with the tissue. The modified tip configuration may include the implantation tool distal end 24 (i.e., the patient-facing terminus of the implantation tool 4) having a non-uniform inner diameter throughout the cavity 20. For example, the implantation tool tip 26 can exhibit a reduced inner diameter that enables flexing of the tines 8 and/or tine tips 9a such that they better align with the axis 3. Thus, the cavity 20 can have at least two inner diameters of $ID_1$ and $ID_2$. $ID_1$ denotes the inner diameter at the implantation tool tip 26, and $ID_2$ denotes the inner diameter within the cavity 20 excluding the implantation tool tip 26, where $ID_1$ is less than $ID_2$. The implantation tool 4 can be fabricated from a flexible, resilient material to allow one or both of the inner wall 22 and outer wall 28 of the implantation tool 4 to flex, facilitating slidable motion of the implant 2 through this constricted region of the implantation tool tip 26. (See FIG. 8). Thus, the implantation tool tip 26 can utilize a material that can stretch to permit passage of the implant 2. This is shown in FIG. 8, where a bulged outer diameter, "OD", can be formed due to the stretching of the implantation tool tip 26.

In other embodiments, the implantation tool 4 is part of, or at least connected to, a catheter. Thus, the patient-facing terminus of the implantation tool 4 or the implantation tool distal end 24 may not have a uniform inner diameter throughout a full length of the catheter segment engaging with the implant 2.

Figure 4:
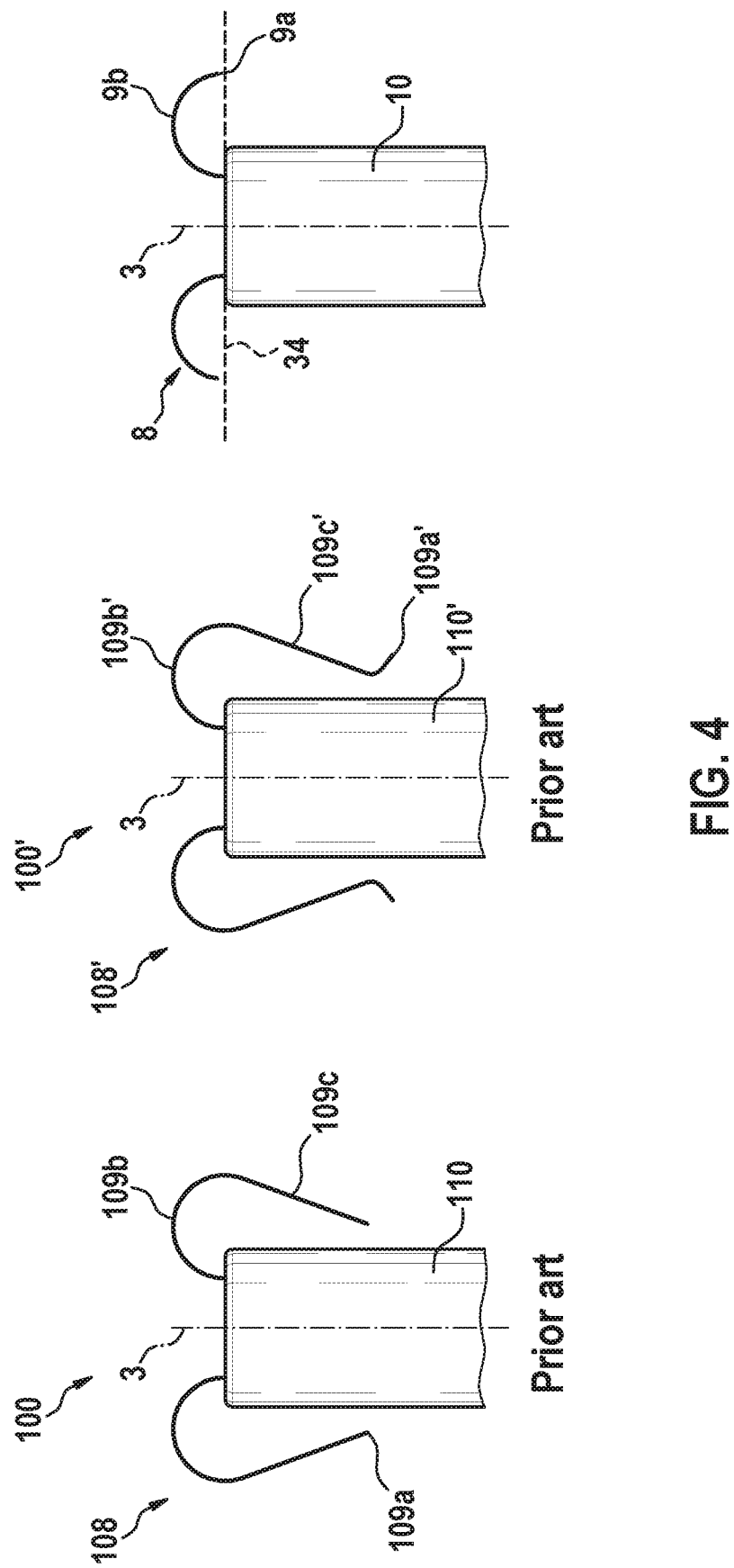
FIG. 4 illustrates prior art implant anchor designs (prior art), as compared to an embodiment of the inventive implant anchoring mechanism.

Contrary to the present invention, prior art tines 108 exhibit a long straightened section 109c to achieve proper alignment (see FIG. 4). Thus, rather than employing lengthy straightened sections within each tine (which undesirably increases the effective length of the device prior to implantation), the implantation tip 26 of the inventive implantation tool 4 has a reduced inner diameter, $D_1$, that can be used to flex the implant's tines 8 to cause them to better align with the axis 3 of the implant 2. Therefore, the tines 8 of the implant 2 can be biased when inserted through the implantation tool 4 so that the tines 8 and/or tine tips 9a are approximately normal with a surface of the tissue into which the tines 8 are inserted during implantation of the implant 2 (i.e., a surface normal to the tissue). In other words, the biasing of the tines 8 with the reduced diameter, $D_1$, implantation tip 26 feature may cause the tine tips 9a to pierce the tissue an angle more closely aligned with the surface normal to the heart. In preferred embodiments, this range of alignment between the axis 3 of the implant and the tine can span between 0 (i.e., coaxial in distal direction) and 45 degrees, with further preference for embodiments offering alignment in the range of 0-20 degrees.

The anchoring mechanism 6 can include at least one tine 8, which may be fabricated from metal. This may include a shape-memory metal, such as nitinol, for example. The tines 8 of the present invention may include various curves, shapes and configurations, and can be generally categorized into four broad embodiments: 1) short tines; 2) flared tines; 3) orthogonally-deployed tines; and, 4) tines that curve in 3 dimensions, such as serpentine tines. However, it is understood that each embodiment is not mutually exclusive and, thus, any embodiment can include any feature of other embodiments.

Figure 3:
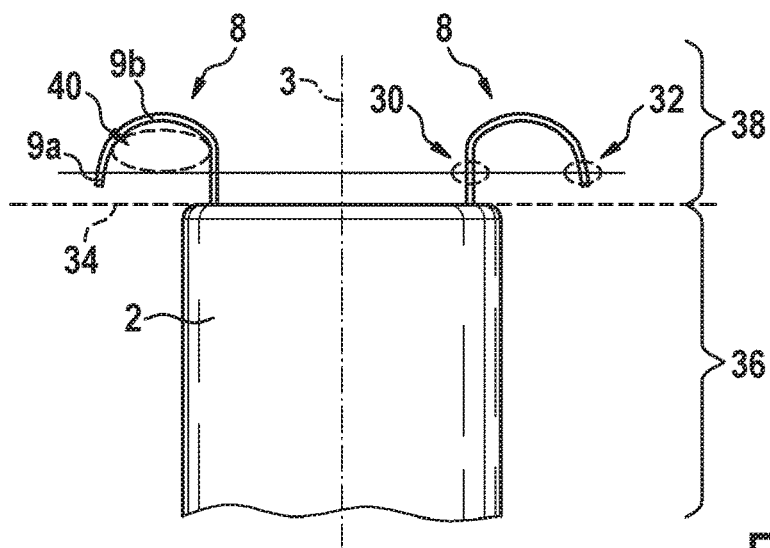
FIG. 3 is a partial cross-sectional view of the implant with the anchoring mechanism anchoring the implant into tissue.

Referring to FIG. 3, generally, each tine 8 is caused to enter the tissue at a first location 30 and then revert back and out from the tissue at a second location 32 such that each tine 8 forms an arch within the tissue, thereby anchoring to the tissue. The reduced diameter of the implantation tool tip 26 can further cause each tine tip 9a to enter the tissue at first locations 30 that are more proximal to the axis 3 so that a distance between each first location 30 and each second location 32 is maximized, thereby generating a stronger anchoring of the tine 8 within the tissue. Thus, with a cylindrical implant casing 2 and tines 8 disposed around a perimeter edge of the implant distal end 18, the tines 8 can be made to enter the tissue at points on a periphery of a smaller diameter circle and exit at points on a periphery of a larger diameter circle. In other words, the tines 8 can be forced to make a more substantial "bite" into the patient's physiology. This more substantial or larger "bite" nominally matches the "bite" that a prior art lengthy tine makes, but the inventive tines 8 achieve this without excess or surplus tine length. Thus, the inventive system 1 can ensure robust fixation while providing the additional benefit of a shorter effective device anchor length. Further, a shorter tine 8 can significantly reduce the risk of instating heart perforation.

Exemplary Short Tine Embodiment

To better understand the benefits and behaviors of the present invention, it may be instructive to first survey the format and behaviors of the prior art leadless pacemaker anchor designs 100, 100'. FIG. 4 shows prior art implant anchor designs ("prior art") 100, 100', as compared to the inventive implant anchoring mechanism shown on the far right. As one can readily observe, the tight curved segments 9b, 109b, 109b' are common to the geometries of all three devices, but the long straightened segments 109c, 109c' of the prior art implant anchors have been stripped from the inventive implant anchor mechanism. For example, the prior art includes a tine 108, 108' that extends from a surface of the casing 110, 110', leading to a curved segment 109b, 109b' having a radius of curvature R, further leading into a straight segment 109c, 109c', and then to a tine tip 109a, 109a'. Contrastingly, the inventive tine 8 extends from a surface of the casing 10, leading to a curved segment 9b having a radius of curvature R, and then to a tine tip 9a. While is it illustrated for there to be no straight segment with the inventive tine 8, some embodiments may include a straight segment between the curved segment 9b and the tine tip 9a, but the straight segment would be shorter as compared to the straight segment of the prior art.

As a non-limiting example, an implant 2 can include a casing 10 with at least one tine 8 extending from an implant distal end 18, in a direction that is approximately parallel to the axis 3, wherein the tine 8 leads into a curved segment 9b having a radius of curvature of R, leading further to the tine tip 9a, wherein the tine tip 9a is facing toward the implant proximal end 16 and is approximately parallel with the axis 3. As indicated above, some embodiments may include a straight segment between the curved segment 9b and the tine tip 9a. In further embodiments, the tine tip 9a may not extend beyond a geometric plane 34 of the implant distal end 18. (See FIG. 3). For example, the geometric plane 34 of the implant distal end 18 can partition the implant 2 into a casing portion 36 and an anchoring portion 38. The anchoring mechanism 6 can be configured so that the tine tips 9a do not extend beyond the geometric plane 34 of the implant distal end 18, and thus do not enter the casing portion 36. In further embodiments, the tine tips 9a do extend beyond the geometric plane 34 of the implant distal end 18 to enter the casing portion 36, but the extension into the casing portion 36 is limited due to the omission of a straight segment, or the inclusion of abridged configuration of a straight segment.

Prior art devices rely on the long straightened segment 109c, 109c' to provide proper alignment, insertion, and adequate implant fixation. For example, the long straightened segments 109c, 109c' of the prior art enable the tines 108, 108' to enter the tissue at an angle better aligned with the surface normal to the patient's heart and then progress deeper into the patient's tissue before the tightly curved segments 109b, 109b' of the tines 108 can form a fixation loop 40 that ultimately anchors the implant into the tissue. A fixation loop 40 is defined herein as an area of tissue caught by the tine 108, 108' when viewed in a cross-sectional view.

The inventive implantation tool tip 26 (see FIG. 2) can have a modified configuration (e.g., reduced inner diameter $ID_1$) that can cause flexing of the short tines 8 for proper alignment before insertion into tissue. If an unmodified implantation tool tip (e.g., a straight tube implantation tool tip without a reduced inner diameter) 126 were to be used with the inventive shortened tines 8, then a smaller fixation loop 40' is generated. FIGS. 5A-5B show the interactions of the prior art and inventive implants using a straight-tube implantation tool tip.

FIG. 5A shows a prior art implantation tool, a prior art implant, and a prior art anchoring mechanism with long tines. Steps 1-3 of FIG. 5A show the interaction of the long tines 108 used with the prior art implantation tool as the prior art implant is being advanced out from the prior art implantation tool and inserted into tissue; where step 1 shows the prior art implant fully seated within the prior art implantation tool; step 2 shows the prior art implant being advanced out from the prior art implantation tool; and step 3 shows the prior art implant anchored to the tissue.

FIG. 5B shows a prior art implantation tool and an inventive implant 2 having the inventive anchoring mechanism 6 with short tines 8. Steps 1-3 of FIG. 5B show the interaction of the inventive short tines 8 used with the prior art implantation tool as the inventive implant 2 is being advanced out from the prior art implantation tool and inserted into tissue; where step 1 shows the inventive implant 2 fully seated within the prior art implantation tool; step 2 shows the inventive implant 2 being advanced out from the prior art implantation tool; and step 3 shows the inventive implant 2 anchored to the tissue.

Step 3 of FIG. 5A shows the ideal anchoring "bite" (or fixation loop 40) into the tissue exhibited by the prior art tine, but also reveals that the long tine segment 109c of the prior art anchoring mechanism is useless following implantation by extending well beyond the tissue back towards the body of the implant, creating excess, unused tine. Step 3 of FIG. 5B shows the comparatively shallow "bite" (or fixation loop 40') into the tissue that would be exhibited by the inventive short tines 8 if used with the prior art implantation tool. It can be seen that the bite exhibited by the long tines 108 in step 3 of FIG. 5A is greater than the bite exhibited by the short tine 8 in step 3 of FIG. 5B. The lack of bite would compromise the stability of the inventive anchor 6. Further, the lack of bite may fail to maintain solid contact between the pacing electrode and tissue and change sensing and stimulation quality.

Step 2 of FIG. 5B readily reveals that each of the short tines 8 would penetrate the tissue at suboptimal angles if the inventive implant 2 and inventive anchoring mechanism 6 were to be used with a prior art implantation tool. Thus, with the prior art implantation tool, the short tines 8 would penetrate the tissue so as to be further removed from the surface normal of the tissue than if longer tines would be used. This is illustrated by the angle of incidence differential between angle A (step 2 of FIG. 5A) for the long tines and angle B (step 2 of FIG. 5B) for the short tines 8. Step 2 of FIG. 5A shows the angle of incidence to be A with use of the prior art implantation tool, the prior art implant, and the prior art longer tines. Step 2 of FIG. 5B shows the angle of incidence to be B with use of the prior art implantation tool, the inventive implant 2, and the inventive shorter tines 8. It can be seen that angle of incidence A is much less than angle of incidence B. The shallower approach angle of the shorter tines 8, paired with the fact that they lack straight segments that would aid in their ability to pierce deeper into the tissue, compromises the shorter tines' 8 ability to generate an adequate fixation loop 40' and "bite" into the tissue. As noted above, this can be seen by a comparison of the fixation loops 40 and 40' between step 3 of FIG. 5A and step 3 of FIG. 5B, respectively.

Figure 6A:
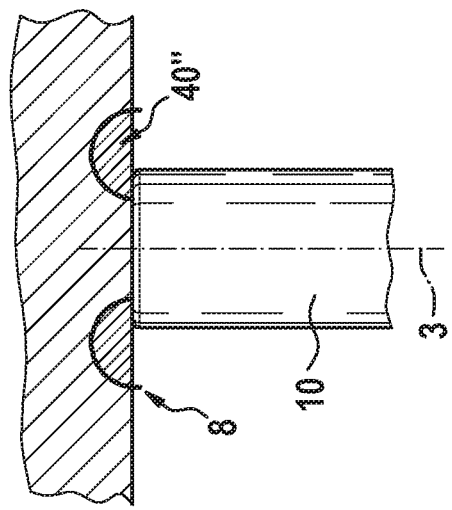
FIGS. 6A-6B show an embodiment of the implant with an embodiment of the anchoring mechanism within a cross-sectional view of an embodiment of the implantation tool, where
Figure 6B:
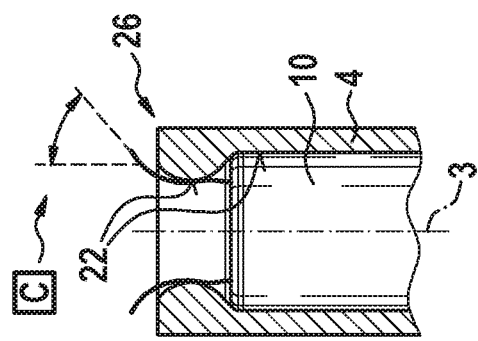
Figure 6C:
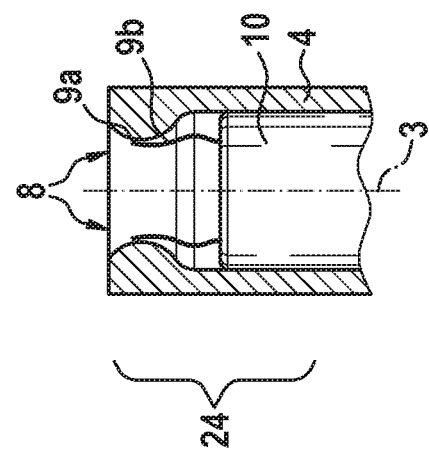
FIG. 6C shows the implant being anchored to tissue.

FIGS. 6A-6C show the interactions of the inventive implant using a modified implantation tool tip to improve the short tine "bite". Referring to FIGS. 6A-6B, the inventive tines 8 and/or tine tips 9a interact with the inner wall 22 of the inventive implantation tool 4 and, in particular, the inner wall 22 at the implantation tool tip 26, so as to be forced to enter the tissue while each tine 8 and/or tine tip 9a is approximately parallel with the axis 3. It is envisioned that during deployment of the implant 2, the implant 2 and the implantation tool 4 would be coaxial so that they both share the same axis 3 extending through the implant distal end 18 and the implantation tool distal end 24. It is further envisioned for the implantation tool distal end 24 to be placed at a surface normal to the tissue during advancement of the implant 2 towards the tissue and during affixment of the implant 2 to the tissue. Thus, the interaction of the tines 8 and/or tine tips 9a with the inner wall 22 of the implantation tool 4 may not only cause each tine 8 and/or tine tip 9a to be approximately parallel with the axis 3, but it can also causes each tine 8 and/or tine tip 9a to be approximately normal to the surface of the tissue when the tine tip 9a makes contact with the surface of the tissue. Note that keeping the tines approximately parallel to the inner wall 22 of the implantation tool also helps with the smooth deployment of the implant 2. As can be readily seen in FIG. 5B, when the inventive short tines 8 are used in a prior art implantation tool 126, the tines can also curve into the inner wall 22 of the inventive implantation tool 4 causing the tines 8 of the implant 2 to snag on the inner wall 22 during implantation. As shown in FIG. 6A, when the tines 8 are kept approximately parallel to the inner wall 22 of the inventive implantation tool 4, then the tines are less apt to dig into the wall and snag when the implant 2 is pushed forward during implantation.

It is further envisioned that with a cylindrical casing 10, each tine 8 exhibits a curve with a radius of curvature R such that each tine tip 9a is positioned to be at a location that is more radially outward from the axis 3 than the position of the emergence of the tine 8 from the casing 10. However, other curvature configurations and trajectories of tine tips 9a can be used. The various configurations and trajectories used may enable the tines 8 to pierce far enough into the tissue to generate a sufficient fixation loop 40" so as to cause the anchoring mechanism 6 "bite" into a substantial amount of the tissue before the curved segments 9b of the tines 8 begin routing their trajectory back toward the implant 2. Further, while the various illustrations in the Figures may show each tine 8 to be a same length, it is understood that any one tine 8 or multiple of tines 8 can be of a different length, thickness, curvature, shape, etc. As noted earlier, the tines 8 are flexed by the implantation tool 4, and as they emerge from the implantation tool 4 and enter the tissue they begin to re-configure back to their preformed shape (see FIG. 6B) so that they can re-configure back to their preformed shape while being routed through the tissue (see FIG. 6C). FIG. 6C shows the preformed shape to be an arch, but other shapes can be used. The flexing from and rebounding to the preformed shape can be achieved by fabricating the tines 8 from a resilient material that allows for flexing without plastic deformation. However, the same can be achieved via shape memory materials as well.

As shown in FIG. 6C, the inventive system 1 may utilize a modified implantation tip 26 to enable the short tine 8 to generate an adequate fixation loop 40'. Thus, overcoming the challenges faced by short tine-based anchor mechanisms 6 can be addressed by narrowing the inner diameter of the implantation tool tip 26 or creating an implantation tool 4 with an implantation tool tip 26 exhibiting an inner diameter of $D_1$. When the implant 2 is fully seated within the implantation tool 4, the inner diameter $D_1$ impinges upon the extended tines 8 and bends them into a state that ensures improved tine/myocardial engagement. (See FIG. 2). In other words, when the implant 2 is fully seated within the cavity 20 (see FIG. 6A), the inner diameter $D_1$ can cause the tines 8 and/or tine tips 9a to be approximately parallel with the axis 3. Thus, the inner diameter $D_1$ may not only force the tines 8 and/or tine tips 9a to enter the tissue at a steeper angle (or approximately normal to a surface of the tissue), it can also cause each tine tip 9a to pierce the tissue at points along a periphery of a tighter circle, as described above. In other words, the inner diameter $D_1$ can further cause each tine tip 9a to enter the tissue at first locations 30 that are more proximal to the axis 3 so that a distance between each first location 30 and each second location 32 is maximized, thereby generating a stronger anchoring of the tine 8 within the tissue. Thus, the inventive short tines 8 can "bite" into the tissue with a fixation loop 40 that is comparable to, and in some cases as large as or larger than the fixation loops demonstrated by prior art anchoring mechanism having longer anchors. Thus, the "bite" of the inventive anchoring mechanism can ensure stable and robust mechanical fixation while enforcing or ensuring viable contact between the pacing/sensing electrode and the heart.

As seen in FIGS. 6A-6C, the implantation tool 4 can have a modified tip 26 to improve the bite of the short tine 8. As noted above, the modified tip 26 can include a reduced inner diameter $ID_1$ to cause the short tines 8 to better align with the axis 3 of the implant 2 as compared to the interaction the short tines 8 would have with an un-modified tip (see FIG. 5B). FIG. 6B clearly shows that the modified tip 26 would facilitate a steeper angle C by which the tines enter the tissue as the inventive implant 2 is advanced from the implantation tool 4. The introduction of the short tines 8 via the steeper angle can allow each short tine 8 to realize a bite into the tissue that is comparable to, if not better than, the bite exhibited in step 3 of FIG. 5A.

While the exemplary embodiment shown in FIG. 2 illustrates the implantation tool distal end 24 having a uniform $D_1$ at the implantation tool tip 26, other implantation tool distal end 24 configurations can be used. For example any one or both of $D_1$ and $D_2$ can be non-uniform. Further, the transition from $D_1$ and $D_2$ can be smooth (i.e., sloped) or non-smooth transition (i.e., stepped).

Figure 7A:
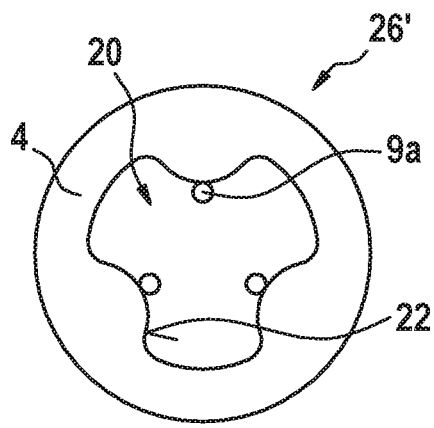
FIGS. 7A-7C show various implantation tool tip configuration, including a double sided ramp feature to seat the tines within notches of the implantation tool, a single sided ramp feature to seat the tines within notches of the implantation tool, and a reduced diameter with scored features that cut an inner wall of the implantation tool back to a main inner diameter, respectively.
Figure 7B:
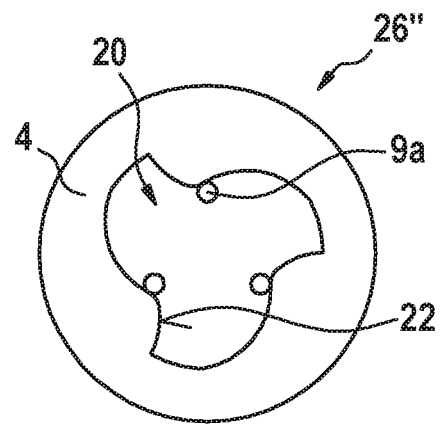
Figure 7C:
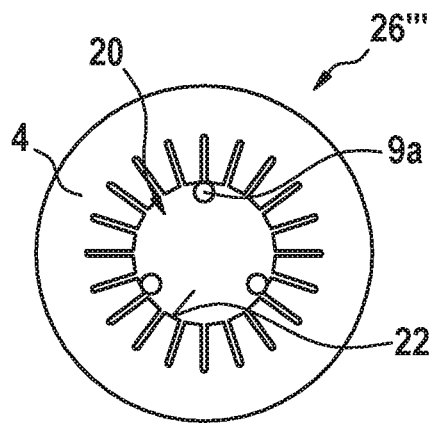

FIGS. 7A-7C show additional implantation tool distal end 24 configurations that may be used with the system 1. The exemplary embodiment of FIGS. 7A-7C is illustrative for an implant design leveraging three tines. However, more of fewer tines could be utilized without departing from the spirit and scope of the present invention. FIG. 7A shows an end view of a tip 26' with a double sided ramp feature to engage the tines 8 within notches along a periphery of a more constricted diameter, which may be $D_1$. As the implant 2 is seated within the cavity 20, each tine 8 may engage with a notch formed on a surface of the inner wall having a diameter $D_1$. Further, each notch may be configured to run along the axis 3 of the implant so that as each tine 8 is caused to flex, a substantial portion of the tine 8 engages the notch. Similar to FIG. 7A, FIG. 7B shows an end view of a tip 26" with a single sided ramp feature to engage the tines 8 within notches along a periphery of a more constricted diameter, which may be $D_1$.

FIG. 7C shows an end view of a tip 26' having an inner wall 22 with a reduced diameter, which may be $D_1$, with scored features (e.g., slits) that cut into the inner wall 22 and extend radially back to a main inner diameter, which may be $D_2$, of the implantation tool 4. The slotted inner wall 22 has enough resiliency to cause the tines 8 to flex when the implant 2 is seated within the cavity 20, but the slotted inner wall 22 may ease the ability to cause the implant 2 to move through the constricted tip 26' with a casing 10 having a diameter that is larger than $D_1$.

As noted above, the implantation tool 4 may be fabricated from a flexible, resilient material, and having the configurations of FIGS. 7A-7C can ease the ability to pass the implant 2 through the implantation tool's cavity 20 and/or tip 26', 26", 26''' because there would be less material to deflect or cause to flex as the implant 2 is forced through the tip 26', 26", 26'''. Thus, as the implant 2 is moved through the cavity 20 and further through the tip 26, the implant 2 would only need to displace a handful of features or portions of the inner wall 22 instead of the entire inner wall 22 of the implantation tool tip 26', 26", 26'''.

It is envisioned for the configurations of FIGS. 7A-7C to require special manufacturing and may present added challenges for transitioning the implant 2 from tethered states back into primary engagements with the implantation tool 4. Such challenges may arise from the need to reseat the tines 8 at points along a targeted inner diameter (e.g., to cause the tines 8 to engage the notches). Depending upon the implantation tool's tip 26', 26", 26''' configuration, such a need might require articulations that rotationally align the implant's 2 and the implantation tool's 4 relative positions in controlled ways. Regardless of the format of the implantation tool tip 26', 26", 26''' and/or catheter tip design used to improve tine alignment and insertion behaviors, the material and/or the configurations of the implantation tool 4 should exhibit properties and/or features that are elastic enough to move out of the way of or be deflected by the iLP body or casing 10 during deployment of the implant 2, but inelastic enough to resist the spring force of the tines 8. Incorporating such a balance within the implantation tool 4 may be a hallmark of some embodiments of the present invention.

Exemplary Flared Tine Embodiment

Figure 9A:
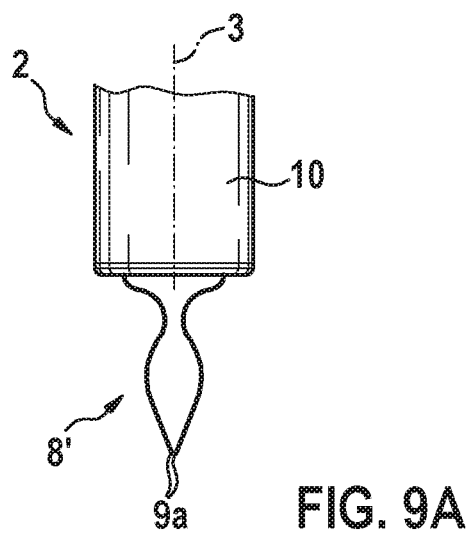
FIGS. 9A-9B show a flared tine embodiment with the tines collapsed together and the tines in a deployed state, respectively.
Figure 9B:
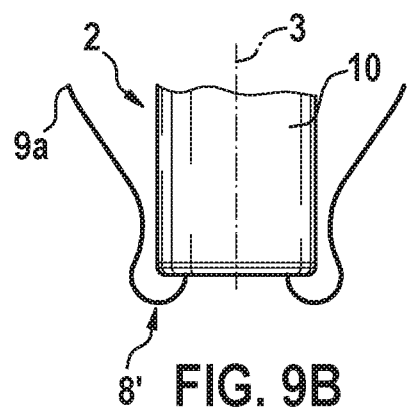

Referring to FIGS. 9A-9B, a flared tine embodiment can include any one tine 8' or a plurality of tines 8' having a flared shape. As noted above, the implantation tool 4 may be part of, or at least connected to, a catheter, where the catheter slides over the implant 2 in a manner described above. The flared tine 8' may allow for easy recapture with the catheter, which may be achieved by the tine tips 9a flaring away from the iLP body or casing 10 so as to not get hung up on the advancing catheter when the tines 9a are in a deployed state. (See FIG. 9B). For example, a user may want to engage and re-engage the implant 2 more than once so it may be beneficial to facilitate easy recapture. The flared shape may also prevent digging into a sheath wall of the catheter when the tines 8' are collapsed and pushed distally within the protective sheath (e.g., when in a catheter). (See FIG. 9A). As seen in FIG. 9A, the flared tines 8' have been collapsed by being forced to abut each other. In a collapsed state, each tine 8' may be flexed so that each tine tip 9a comes closer to or even makes contact with another tine tip 9a at a connecting point. This connecting point may be at a point along the axis 3. When the tine tips 9a come close together to form the collapsed state, each tine tip 9a is at or near the connecting point, and is thus far removed from the sheath wall of any catheter being inserted over the implant 2. Another advantage may be that if any one of the tines 8' fail to enter the tissue during deployment, the extended flare shaped tine 8' can still get captured within or anchor to trabeculae tissue to ensure a secure fixation. Anchoring to trabeculae tissue may provide enough securement to enable adequate fixation for the instillation of the implant 2.

Exemplary Orthogonally Deployed Tines

Figure 10A:
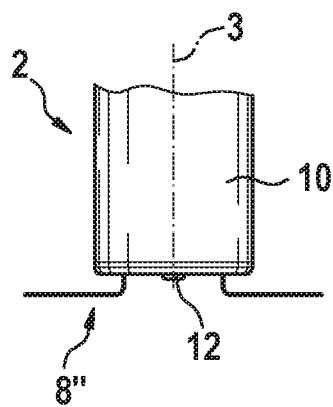
FIGS. 10A-10C show an orthogonally-deployed tine embodiment with long tines, short tines, and tines with anti-dislodgement barbs, respectively.
Figure 10B:
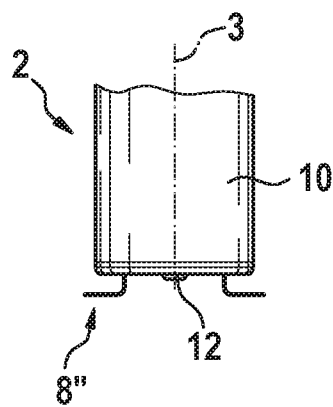
Figure 10C:
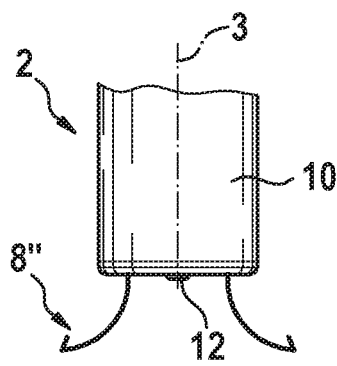

FIGS. 10A-10C show tines that deploy orthogonal to the axis of the implant ("orthogonally-deployed tines") 8" when in a deployed state. With the orthogonally-deployed tines 8", any one tine 8" or any number of tines 8" can have a wide range of lengths within a range from shorter than the short tines 8 described above to longer than the long tines disclosed by the prior art. Thus, with the orthogonally-deployed tines 8", the tines 8" may have total exposed lengths similar to those explored in other designs within this write-up, or they might potentially employ shorter exposed lengths (e.g., 3-4 mm). To enable deployment orthogonal to the axis 3 of the implant 2, the curvature of the tine 8" within the curved segment 9b may be a 90 degrees curve with a radius, but may also be sharp or high (i.e., have a low radius of curvature) so as to form an approximate ninety-degree angle. Thus, each tine 8" may extend from the implant distal end 18 to be parallel with the axis 3 and then lead into the approximate ninety-degree angle curved segment to extend radially outward from the axis 3. The extension radially outward may be a straight segment so that the tine 8" forms a general "L" shape. When deployed, the tines 8" can curve approximately ninety degrees as referenced against the fully straightened orientation needed for transit through the vasculature. By orienting each straight segment of each tine 8" radially from the central axis or axis 3 of the implant 2 they can serve to lock or anchor the implant 2 within the tissue. In other words, the tines 8" can be caused to flex towards each other so that each tine 8" and/or tine tip 9a is parallel with the axis 3, as described above. As the implant 2 is advanced towards the tissue, the tines 8" again re-configure to their preformed shape, as described above. Instead of circling back out of the tissue, the tips 9a of the orthogonally-deployed tines 8" can remain within the tissue to achieve anchoring and deployment of the implant 2. Further, by orientating each straight segment of a tine 8" to extend radially in a direction opposing a straight segment of another tine 8", the tines 8" can serve to anchor the implant 2 within the tissue that is being subjected to stresses induced by impinging blood flow and/or heart contractions.

As noted above, the tines 8" can include a long straight segment, which may provide a means for embedding the anchor mechanism into a substantial portion of the myocardium and ensure robust fixation. Further, the approximate ninety-degree curved segment leading to straight tine segments may be configured so that the straight segments of each tine 8" extends in opposing directions from each other. This opposing-directional configuration can facilitate a mechanical separation of each tine tip 9a from the electrode 12 of the implant 2. For instance, if the implant 2 is a leadless pacemaker, the electrode 12 may extend from a central portion of the implant distal end 18. Ensuring and/or maximizing mechanical separation of each tine tip 9a from the electrode 12 may reduce the chances of tissue/myocardium interactions occurring at the tine tip 9a from impacting or influencing pacing capture thresholds. Alternatively, some embodiments can use or leverage shorter straight segments to make the delivery system 1 easier. For example, shorter straight segments may facilitate use of a smaller cup or implant distal end 24 to contain the iLP or implant 2 and to straighten or flex the tines 8" during the installation procedure. Further, shorter tines may be less traumatic to tissue than longer tines. Further embodiments can include small barb features (i.e., anti-dislodgement bars) formed into and/or onto the any one or multiple of tines 8" and/or tine tips 9a, as shown in FIG. 10C.

Exemplary Serpentine Tines

Figure 11A:
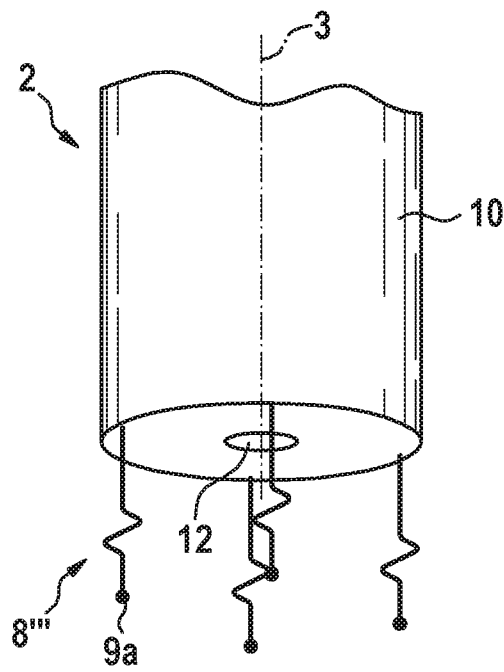
FIGS. 11A-11C show various embodiments of serpentine tines with spheroid shape tips, unidirectional barbed tips, and hooked end tips, respectively.
Figure 11B:
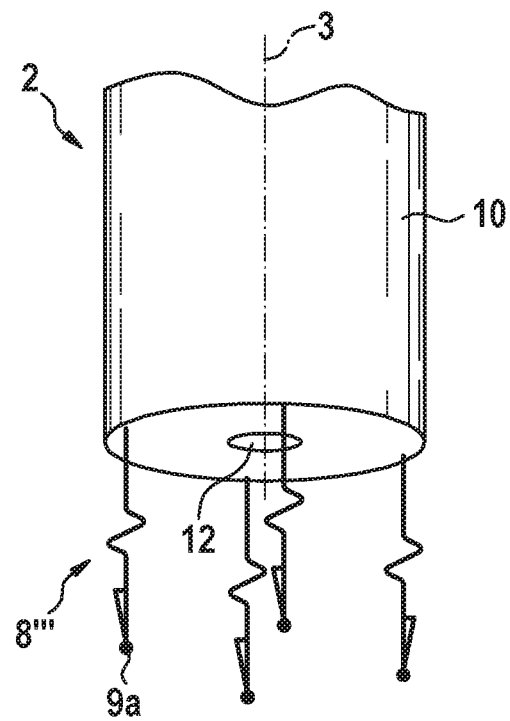
Figure 11C:
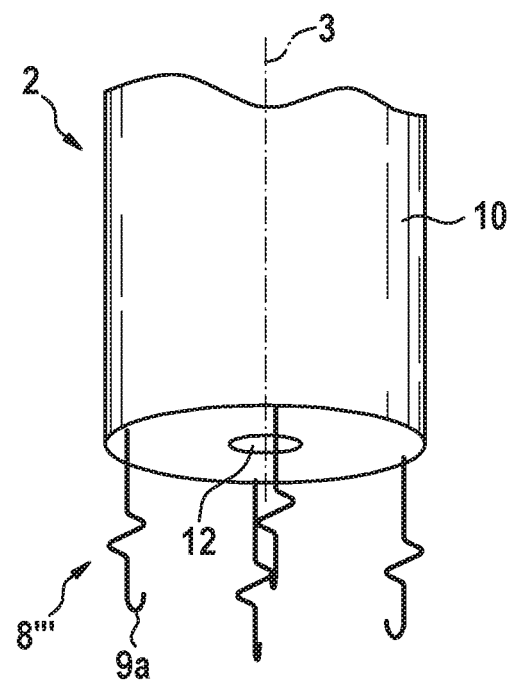

FIGS. 11A-11C show various embodiments of serpentine tines 8''' that may be used with the system. These serpentine tines demonstrate one embodiment of a more general tine class manifesting a 3-dimensional design format. As shown in the Figures, the straightened nature of these anchor types represent the configuration observed when the tines reside within the catheter tip (not shown). Once deployed, these tines would, akin to the tine types discussed in the remainder of this filing, adopt an arched trajectory within the myocardium. Any one tine 8''' or multiple of tines 8''' can extend from the implant distal end 18 to run approximately parallel with the axis 3. Any one tine 8' or multiple of tines 8' can exhibit a serpentine shape. This may be done to facilitate anchoring the implant 2 into tissue in a less-destructive or non-destructive manner by the serpentine shape spreading the tissue fibers during tine 8' insertion. The serpentine shape can also enabling scar tissue that forms around the tine 8" to enhance securement of the tine 8''' within the tissue and enhance anchoring of the implant 2. Further atraumatic tine tip 9a geometries, such as a ball or other spheroid shape, for example, can be used to further reduce or prevent trauma that may otherwise be caused due to movement of tine tip 9a relative to the tissue (see FIG. 11A). FIG. 11B shows a tine tip 9a geometry including a unidirectional barb, which may resists retraction or inhibit dislodgement of the implant 2 after being anchored to the tissue. FIG. 11C shows a tine tip 9a geometry that includes hooked ends. The curved portion of the hook can provide a rounded end to spearhead insertion and thus deliver an atraumatic insertion, while the hook can provide a unidirectional force or gripping feature to further retain the implant 2 (i.e., resist retraction or inhibit dislodgement). It is envisioned for three to four tines 8''' to be used with such embodiments, but any number of tines 8''' can be used. It is further envisioned for each tine 8''' to be equidistally spaced about a perimeter edge of the casing distal end 18; however, the tines 8''' can be positioned to extend from any casing 10 surface location and be separated by any distance, whether equally separated or not. Thus, the number of tines 8''', the spacing of tines 8''', the length of tines 8''', and the placement of tines 8''' can be varied to optimize total retention force.

In general, a method of deploying the implant 2 that is a leadless pacemaker with the system 1 may include: 1) choosing a jugular venous or femoral venous and opening the jugular or femoral venous to create a venous access through which the implant is to be deployed; 2) placing an introducer and passing through a preloaded leadless pacemaker 2 using a steerable catheter via an introducer; 3) determining an appropriate implant site using a fluoroscope, which may include testing for pacing ability when possible; 4) placing the implantation tool distal end 24 against the tissue of the heart so as to be normal to a surface of the tissue; 5) advancing the leadless pacemaker 2 towards the tissue so as to cause the tine tips 9a of the tines 8 of the leadless pacemaker 2 to enter the tissue normal to the surface of the tissue; 6) allowing the tines 8 to rebound to their preformed shape as they are inserted into the tissue due to further advancement of the leadless pacemaker 2 towards the tissue, thereby anchoring the leadless pacemaker 2 to the tissue and deploying the leadless pacemaker 2; 7) tethering the leadless pacemaker 2, which may include testing and confirming that a secure anchor has been achieved; 8) removing the tether, the implantation tool 4, and the introducer from the venous access; and, 9) closing the venous access.

The present invention applies an effective change to leadless pacemaker implantation tooling that facilitates the effective shortening of the implant's anchoring mechanism 6. This tooling modification introduces no new or additional procedural steps in the implantation process and improves the risk profile for therapies reliant upon tine-based anchoring. Because the bulk of a tine-based anchor's ability to stably affix an implant 2 to the patient's anatomy depends upon the trajectory of the tine 8 routing through the myocardium and the present invention maintains the same such trajectory as is offered by prior art designs, the shortened tines 8 serve to reduce the footprint of the anchoring mechanism 6 without compromising mechanical anchoring robustness. Further, because extraneous material can be removed from the tine geometry, the inventive anchoring mechanism 6 introduces less foreign material into the patient's anatomy, thus reducing opportunities for the implant 2 to become encapsulated and, in-turn, potentially aiding in long term explantation capabilities.

As noted above, the long straight segment of the prior art tine only aids in improved implant/patient interfacing while the implant is being installed by improving the approach angle. The present invention, however, exploits a specially configured implantation tool tip 26, rather than focusing on the tine configuration to achieve the desired approaching angle. This shifted allocation means that the component of the system 1 exclusively used for implantation—the implantation tool 4—performs an enhanced duty that frees up design flexibility for the anchoring mechanism 6 and the implant 2. In other words, the anchoring mechanism 6 is no longer forced to include added hardware (i.e., the extended portions of the tines or the lengthy straightened segments) that are only beneficial during implantation procedures and otherwise non-functional thereafter. As noted earlier, shorter anchors or tines 8 ease the challenge in routing an implant 2 from the IVC into the heart, ease the competition for precious space needed to power the implant 2, and reduce the potential for the implant 2 to grossly perforate the patient's heart.

By routing a shorter tine 8 through the myocardium (and not having to drag longer straightened portions of the tine along for the ride), the damage to patient tissue at the anchoring site may be reduced. Such reductions would arrive with potential gains for lowering capture thresholds that would, in-turn, improve realizable service times.

As an ancillary benefit to the disclosed invention, embodiments with a rounded catheter tip (e.g., a more bulbous format) can further reduce the chances that the catheter itself will problematically scrap against the patient anatomy when entering the heart from the IVC. This approach contrasts with catheter designs of the prior art that generally include a cut-off tube leading to the patient's vasculature. These cut-off tube designs introduce a firm inner edge within a patient physiology, capable of inducing trauma. The revised geometry (especially when paired with soft material selection) of the present invention can further reduce risks to the patient during leadless implant procedures.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A system for installation of a leadless implant in a living body, comprising:
    a leadless implant, comprising:
        a casing having a casing distal end and a casing proximal end forming an axis that runs from the casing proximal end to the casing distal end, wherein the casing houses electrical components configured to provide electrical pulses to the living body and/or to sense physiological signals from the mammal body; and,
        an anchoring mechanism comprising at least one tine extending from the surface of the casing, leading to a curved segment, and then directly to a tine tip, wherein the at least one tine comprises a flexible, resilient material; and
    an implantation tool, comprising:
        a sleeve member having a cavity and a sleeve tip both formed by an inner wall, wherein the inner wall at the sleeve tip has an inner diameter of $D_1$ and the inner wall at the cavity has an inner diameter of $D_2$, wherein $D_1$ is less than $D_2$;
        wherein the implantation tool is configured to slidably receive the leadless implant through the cavity;
    wherein $D_1$ causes the at least one tine to flex inward when a portion of the at least one tine makes contact with the inner wall for alignment of the at least one tine prior to contact with bodily tissue, and
    wherein a transition from the diameter $D_1$ to the diameter $D_2$ is stepped.

2. The system recited in claim 1, wherein the implantation tool is at least a part of a catheter and connected to a catheter.

3. The system recited in claim 1, wherein the implantation tool comprises a flexible, resilient material so that at least the inner wall of the sleeve tip is deflectable.

4. The system recited in claim 1, wherein the curved section of any tine has at least one curve, which is at least segmentally formed in 3 dimensions.

5. The system recited in claim 1, wherein the diameter $D_1$ causes the at least one tine to enter the bodily tissue approximately parallel to an axis of the implantation tool.

6. The system recited in claim 1, wherein the diameter $D_1$ causes the at least one tine to be approximately normal to a surface of the bodily tissue when the at least one tine makes contact with the surface of the bodily tissue.

7. The system recited in claim 1, wherein a transition from the diameter $D_1$ to the diameter $D_2$ is smooth.

8. The system recited in claim 1, wherein the inner wall of the sleeve tip is formed by a double sided ramp forming the diameter $D_1$ at a more constricted portion of the double sided ramp and forming the diameter $D_2$ at a main diameter of the inner wall.

9. The system recited in claim 1, wherein the curved segment of the at least one tine forms an approximate ninety-degree angle so that a portion of the at least one tine leading to the tine tip extends radially outward from an axis of the implantation tool.

10. The system recited in claim 1, wherein the at least one tine has a flared shape after the curved segment to cause the at least one tine leading to the tine tip to flare away from the casing.

11. The system recited in claim 1, wherein the at least one tine has a spheroid shape tine tip.

12. A system for installation of a leadless implant in a living body, comprising:
- a leadless implant, comprising:
  - a casing having a casing distal end and a casing proximal end forming an axis that runs from the casing proximal end to the casing distal end, wherein the casing houses electrical components configured to provide electrical pulses to the living body and/or to sense physiological signals from the mammal body; and,
  - an anchoring mechanism comprising at least one tine extending from the surface of the casing, leading to a curved segment, and then directly to a tine tip, wherein the at least one tine comprises a flexible, resilient material; and
- an implantation tool, comprising:
  - a sleeve member having a cavity and a sleeve tip both formed by an inner wall, wherein the inner wall at the sleeve tip has an inner diameter of $D_1$ and the inner wall at the cavity has an inner diameter of $D_2$, wherein $D_1$ is less than $D_2$;
  - wherein the implantation tool is configured to slidably receive the leadless implant through the cavity;
- wherein $D_1$ causes the at least one tine to flex inward when a portion of the at least one tine makes contact with the inner wall for alignment of the at least one tine prior to contact with bodily tissue,
- wherein the inner wall of the sleeve tip is formed by a single sided ramp forming the diameter $D_1$ at a more constricted portion of the double sided ramp and forming the diameter $D_2$ at a main diameter of the inner wall, and
- wherein the inner wall of the sleeve tip forms $D_1$ and at least one slit extends radially from $D_1$ to the main diameter $D_2$.

13. A system for installation of a leadless implant in a living body, comprising:
- a leadless implant, comprising:
  - a casing having a casing distal end and a casing proximal end forming an axis that runs from the casing proximal end to the casing distal end, wherein the casing houses electrical components configured to provide electrical pulses to the living body and/or to sense physiological signals from the mammal body; and,
  - an anchoring mechanism comprising at least one tine extending from the surface of the casing, leading to a curved segment, and then directly to a tine tip, wherein the at least one tine comprises a flexible, resilient material; and
- an implantation tool, comprising:
  - a sleeve member having a cavity and a sleeve tip both formed by an inner wall, wherein the inner wall at the sleeve tip has an inner diameter of $D_1$ and the inner wall at the cavity has an inner diameter of $D_2$, wherein $D_1$ is less than $D_2$;
  - wherein the implantation tool is configured to slidably receive the leadless implant through the cavity;
- wherein $D_1$ causes the at least one tine to flex inward when a portion of the at least one tine makes contact with the inner wall for alignment of the at least one tine prior to contact with bodily tissue, and
- wherein the inner wall of the sleeve tip comprises at least one notch formed on a surface of the inner wall having $D_1$.

14. A system for installation of a leadless implant in a living body, comprising:
- a leadless implant, comprising:
  - a casing having a casing distal end and a casing proximal end forming an axis that runs from the casing proximal end to the casing distal end, wherein the casing houses electrical components configured to provide electrical pulses to the living body and/or to sense physiological signals from the mammal body; and,
  - an anchoring mechanism comprising at least one tine extending from the surface of the casing, leading to a curved segment, and then directly to a tine tip, wherein the at least one tine comprises a flexible, resilient material; and
- an implantation tool, comprising:
  - a sleeve member having a cavity and a sleeve tip both formed by an inner wall, wherein the inner wall at the sleeve tip has an inner diameter of $D_1$ and the inner wall at the cavity has an inner diameter of $D_2$, wherein $D_1$ is less than $D_2$;
  - wherein the implantation tool is configured to slidably receive the leadless implant through the cavity;
- wherein $D_1$ causes the at least one tine to flex inward when a portion of the at least one tine makes contact with the inner wall for alignment of the at least one tine prior to contact with bodily tissue, and
- wherein the sleeve member includes an outer diameter that remains constant along a length of the sleeve member.

15. The system recited in claim 14, wherein the implantation tool is at least a part of a catheter and connected to a catheter.

16. The system recited in claim 14, wherein the implantation tool comprises a flexible, resilient material so that at least the inner wall of the sleeve tip is deflectable.

17. The system recited in claim 14, wherein the curved section of any tine has at least one curve, which is at least segmentally formed in 3 dimensions.

18. The system recited in claim 14, wherein the diameter $D_1$ causes the at least one tine to enter the bodily tissue approximately parallel to an axis of the implantation tool.

19. The system recited in claim 14, wherein the diameter $D_1$ causes the at least one tine to be approximately normal to a surface of the bodily tissue when the at least one tine makes contact with the surface of the bodily tissue.

20. The system recited in claim 14, wherein a transition from the diameter $D_1$ to the diameter $D_2$ is smooth.

21. The system recited in claim 14, wherein the inner wall of the sleeve tip is formed by a double sided ramp forming the diameter $D_1$ at a more constricted portion of the double sided ramp and forming the diameter $D_2$ at a main diameter of the inner wall.

22. The system recited in claim 14, wherein the curved segment of the at least one tine forms an approximate ninety-degree angle so that a portion of the at least one tine leading to the tine tip extends radially outward from an axis of the implantation tool.

23. The system recited in claim 14, wherein the at least one tine has a flared shape after the curved segment to cause the at least one tine leading to the tine tip to flare away from the casing.

24. The system recited in claim 14, wherein the at least one tine has a spheroid shape tine tip.

* * * * *